United States Patent
Zon

(10) Patent No.: US 8,715,938 B2
(45) Date of Patent: *May 6, 2014

(54) REVERSIBLE DI-NUCLEOTIDE TERMINATOR SEQUENCING

(75) Inventor: Gerald Zon, San Carlos, CA (US)

(73) Assignee: Life Technologies Corporation, Carlsbad, CA (US)

(*) Notice: Subject to any disclaimer, the term of this patent is extended or adjusted under 35 U.S.C. 154(b) by 70 days.

This patent is subject to a terminal disclaimer.

(21) Appl. No.: 13/198,901

(22) Filed: Aug. 5, 2011

(65) Prior Publication Data

US 2013/0065225 A1 Mar. 14, 2013

Related U.S. Application Data

(63) Continuation of application No. 12/275,161, filed on Nov. 20, 2008, now Pat. No. 8,017,338.

(60) Provisional application No. 61/003,889, filed on Nov. 20, 2007.

(51) Int. Cl.
*C12Q 1/68* (2006.01)
*C12P 19/34* (2006.01)
*C07H 21/04* (2006.01)

(52) U.S. Cl.
USPC ... 435/6.12; 435/91.2; 536/24.31; 536/24.32; 536/24.33

(58) Field of Classification Search
None
See application file for complete search history.

(56) References Cited

U.S. PATENT DOCUMENTS

| | | |
|---|---|---|
| 4,439,356 A | 3/1984 | Khanna et al. |
| 4,481,136 A | 11/1984 | Khanna et al. |
| 4,933,471 A | 6/1990 | Lee |
| 5,066,580 A | 11/1991 | Lee |
| 5,185,144 A | 2/1993 | Koslo |
| 5,188,934 A | 2/1993 | Menchen et al. |
| 5,231,191 A | 7/1993 | Woo et al. |
| 5,302,509 A | 4/1994 | Cheeseman |
| 5,366,860 A | 11/1994 | Bergot et al. |
| 5,378,841 A | 1/1995 | Summerton |
| 5,432,272 A | 7/1995 | Benner |
| 5,436,134 A | 7/1995 | Haugland et al. |
| 5,470,967 A | 11/1995 | Huie |
| 5,654,442 A | 8/1997 | Menchen et al. |
| 5,698,685 A | 12/1997 | Summerton et al. |
| 5,719,262 A | 2/1998 | Buchardt et al. |
| 5,750,409 A | 5/1998 | Herrmann et al. |
| 5,763,594 A | 6/1998 | Hiatt et al. |
| 5,800,996 A | 9/1998 | Lee et al. |
| 5,817,781 A | 10/1998 | Swaminathan |
| 5,840,999 A | 11/1998 | Benson et al. |
| 5,847,162 A | 12/1998 | Lee et al. |
| 5,863,727 A | 1/1999 | Lee et al. |
| 5,863,753 A | 1/1999 | Haugland et al. |
| 5,908,755 A | 6/1999 | Kumar et al. |
| 5,936,087 A | 8/1999 | Benson et al. |
| 5,945,526 A | 8/1999 | Lee et al. |
| 6,005,113 A | 12/1999 | Wu et al. |
| 6,008,379 A | 12/1999 | Benson et al. |
| 6,017,712 A | 1/2000 | Lee et al. |
| 6,025,505 A | 2/2000 | Lee et al. |
| 6,051,719 A | 4/2000 | Benson et al. |
| 6,080,852 A | 6/2000 | Lee et al. |
| 6,080,868 A | 6/2000 | Lee et al. |
| 6,087,095 A | 7/2000 | Rosenthal et al. |
| 6,111,116 A | 8/2000 | Benson et al. |
| 6,127,121 A | 10/2000 | Meyer et al. |
| 6,143,877 A | 11/2000 | Meyer et al. |
| 6,232,465 B1 | 5/2001 | Hiatt et al. |
| 6,248,884 B1 | 6/2001 | Lam et al. |
| 6,306,597 B1 | 10/2001 | Macevicz et al. |
| 6,632,655 B1 | 10/2003 | Mehta et al. |
| 6,664,079 B2 | 12/2003 | Ju et al. |
| 7,057,026 B2 | 6/2006 | Barnes et al. |
| 7,060,440 B1 * | 6/2006 | Kless ............................ 435/6.1 |
| 8,017,338 B2 * | 9/2011 | Zon ............................. 435/6.12 |
| 2002/0119448 A1 * | 8/2002 | Sorge et al. ...................... 435/6 |
| 2007/0172873 A1 | 7/2007 | Brenner et al. |
| 2009/0263797 A1 | 10/2009 | Zon |

FOREIGN PATENT DOCUMENTS

| | | |
|---|---|---|
| EP | 0050684 | 5/1982 |
| WO | 91/06678 | 5/1991 |
| WO | 92/20702 | 11/1992 |
| WO | 96/04405 | 2/1996 |
| WO | 97/36960 | 10/1997 |
| WO | 98/22489 | 5/1998 |
| WO | 98/39352 | 9/1998 |
| WO | 99/14226 | 3/1999 |
| WO | 99/16832 | 4/1999 |

(Continued)

OTHER PUBLICATIONS

Adelfinskaya, O et al., "Polymerase-catalyzed synthesis of DNA from phosphoramidate conjugates of deoxynucleotides and amino acids", *Nuc Acids Res*,, vol. 35(15), pp. 5060-5072 (2007).

Ambramova, T et al., "A facile and effective synthesis of dinucleotide 5'-triphosphates", *Biorganic & Medicinal Chemistry*, vol. 15, pp. 6549-6555 (2007).

Ambramova, T et al., "Design and sysnthesis of dinucleotide 5'-triphosphates with expanded functionality", *Bioorganic & Med Chemistry*, (2008).

(Continued)

*Primary Examiner* — Prabha Chunduru

(57) ABSTRACT

The present teachings provide methods, compositions, and kits for synthesizing and sequencing nucleic acids. In some embodiments, reversible di-nucleotide compounds are employed along with cleaving reactions that remove a label and a blocking moiety. Improved sequencing efficiency is achieved by the rapid polymerase-mediated incorporation of reversible di-nucleotide compounds. In some embodiments, the di-nucleotides do not contain conventional nucleotide triphosphates, but rather employ amino acid phosphoramidate nucleotides (AAPNs).

16 Claims, 6 Drawing Sheets

(56) References Cited

FOREIGN PATENT DOCUMENTS

| WO | 99/27020 | 6/1999 |
|---|---|---|
| WO | 00/50642 | 8/2000 |
| WO | 00/53805 | 9/2000 |
| WO | 01/16366 | 3/2001 |
| WO | 01/38584 | 5/2001 |
| WO | 03/002767 | 1/2003 |
| WO | 2006/084132 | 8/2006 |
| WO | 2007/020457 | 2/2007 |
| WO | 2007/121489 | 10/2007 |

OTHER PUBLICATIONS

Caruthers, M, "Chemical Synthesis of DNA and DNA Analogues", *Acc. Chem. Res, 24*, pp. 278-284 (1991).

Fasman, Gerald D., "UV Spectral Characteristics and Acidic Dissociation Constants of 280 Alkyl Bases. Nucleosides and Nucleotides", *Practical Handbook of Biochemistry and Molecular Biology*, CRC Press, Boca Raton, FL, pp. 385-394 (1989).

Flanagan, J et al., "Functionalized Tricarbocyanine Dyes as near-Infrared Fluorescent Probes for Biomolecules", *Bioconjug. Chem.*, vol. 8, pp. 751-756 (1997).

Freier, S et al., "The ups and downs of nucleic acid duplex stability: structure-stability studies on chemically-modified DNA:RNA duplexes", *Nucleic Acids Research*, vol. 25(22), pp. 4429-4443 (1997).

Fujimori, S. et al., "Enantio-DNA Recognizes Complimentary RNA but Not Complementary DNA", *J. Am. Chem. Soc.*, vol. 112, pp. 7436-7438 (1990).

Garbesi, A. et al., "L-DNAs as potential antimessenger oligonucleotides: a reassessment", *Nucleic Acids Research*, vol. 21(18), 1993, pp. 4159-4165.

Jones, et al., "Synthesis and Binding Properties of Pyrimidine Oligodeoxynucleoside Analogs Containing Neutral Phosphodiester Replacements.", *J. Org. Chem.*, vol. 58, pp. 2983-2991 (1993).

Ju, J et al., "Four-color DNA sequencing by synthesis using cleavable fluorescent nucleotide reversible terminators", *PNAS*, vol. 103 (52), 2006, pp. 19635-19640.

Lee, L G. et al., "New energy transfer dyes for DNA sequencing", *Nucleic Acids Research*, vol. 25,(14), pp. 2816-2822 (1997).

Lee, L. G. et al., "DNA Sequencing with Dye-Labeled Terminators and T7 DNA Polymerase: Effect of Dyes and dNTPs on Incorporation of Dye-Terminators and Probability Analysis of Termination Fragments", *Nucleic Acids Res.*, vol. 20(10), pp. 2471-2483 (1992).

Ludwig, J et al., "Rapid and Efficient Synthesis of Nucleoside 5'-O-(1-Thiotriphosphates), 5'-Triphosphates and 2',3'-Cyclophosphorothioates Using 2-Chloro-4H-1,3,2-benzodioxaphosphorin-4-one", *J Org Chem*, vol. 54, pp. 631-635 (1989).

Nielsen, Peter E. et al., "Sequence-Selective Recognition of DNA by Strand Displacement with a Thymine-Substituted Polyamide", *Science*, vol. 254(5037), pp. 1497-1500 (1991).

Rosenblum, B B. et al., "New dye-labeled terminators for improved DNA sequencing patterns", *Nucleic Acids Research*, vol. 25(22), pp. 4500-4504 (1997).

Sauer, M. et al., "New Fluorescent Dyes in the Red region for Biodiagnostics", *Journal of Fluorescence*, vol. 5(3), pp. 247-261 (1995).

Stirchak, et al, "Uncharged stereoregular nucleicacid analogues. 1. Synthesis of a Cytosine containino oliaomerwith carbamate intemucleoside linkages", *J. Org.Chem*, vol. 52, pp. 4202-4206 (1987).

Urata, H. et al, "Spectroscopic Characterization of Heterochiral DNAs", Nucleic Acids Symposium Series No. 29, pp. 69-70 (1993.

PCT/US2008/084242 International Search Report Mailed May 4, 2009.

PCT/US2008/084242 International Preliminary Report on Patentability mailed Jun. 30, 2010.

Vasseur, et al, "Oligonucleosides: Synthesis of a Novel Methylhydroxylamine-Linked Nucleoside Dimer and Its Incorporation into Antisense Sequences", *J. Am. Chem. Soc.*, vol. 144), pp. 4006-4007 (1992).

Wu, J et al., "Termination of DnA synthesis by N6-alkylated, not 3'-O-alkylated, photocleavable 2'-deoxyadenosine triphosphates", *Nuc Acids Research*, vol. 35(19), pp. 6339-6349 (2007).

* cited by examiner

| Group A | Group G | Group C | Group T |
|---|---|---|---|
| 3' AA 5'<br>Blocker  Dye 1 | 3' AG 5'<br>Blocker  Dye 1 | 3' AC 5'<br>Blocker  Dye 1 | 3' AT 5'<br>Blocker  Dye 1 |
| 3' TA 5'<br>Blocker  Dye 2 | 3' TG 5'<br>Blocker  Dye 2 | 3' TC 5'<br>Blocker  Dye 2 | 3' TT 5'<br>Blocker  Dye 2 |
| 3' CA 5'<br>Blocker  Dye 3 | 3' CG 5'<br>Blocker  Dye 3 | 3' CC 5'<br>Blocker  Dye 3 | 3' CT 5'<br>Blocker  Dye 3 |
| 3' GA 5'<br>Blocker  Dye 4 | 3' GG 5'<br>Blocker  Dye 4 | 3' GC 5'<br>Blocker  Dye 4 | 3' GT 5'<br>Blocker  Dye 4 |

C-21; R=CCCH$_2$NHCOCF$_3$

U-26; R=CCCH$_2$NHCOCF$_3$

A-37; R=CCCH$_2$NHCOCF$_3$

G-42; R=CCCH$_2$NHCOCF$_3$

SEQUENCE LISTING

```
<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaactgcagc cttaaggcga tgtctcactg ccg                                    33

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aactgcagcc ttaaggcgat gtctcactgc cg                                     32
```

REVERSIBLE DI-NUCLEOTIDE TERMINATOR SEQUENCING

CROSS-REFERENCE TO RELATED APPLICATIONS

This application is a continuation of U.S. application Ser. No. 12/275,161 filed Nov. 20, 2008, which is a nonprovisional and claims priority to U.S. provisional application No. 61/003,889, filed Nov. 20, 2007 which disclosures are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Sep. 8, 2010, is named 6907US.txt and is 735 bytes in size.

FIELD

The present teachings generally relate to methods for sequencing nucleic acids.

BACKGROUND

The detection of the presence or absence of (or quantity of) one or more target nucleic acids in a sample or samples containing one or more target sequences is commonly practiced. For example, the detection of cancer and many infectious diseases, such as AIDS and hepatitis, routinely includes screening biological samples for the presence or absence of diagnostic nucleic acid sequences. Also, detecting the presence or absence of nucleic acid sequences is often used in forensic science, paternity testing, genetic counseling, and organ transplantation.

The gold standard in nucleic acid sequencing is capillary electrophoresis employing labeled dideoxy-nucleotides. Recently, next generation sequencing approaches have been described, bearing the promise of increased speed, throughput, and accuracy, and lower cost. Certain of these approaches employ polymerase-mediated incorporation of reversible terminator compounds (see for example U.S. Pat. No. 6,664, 079). Other next-generation sequencing approaches employ ligation-mediated strategies (see for example WO2006/084132). Trade-offs in speed, accuracy, and cost continue to plague next generation sequencing approaches. The present teachings combine the strengths of polymerase-mediated approaches with certain aspects of ligation-mediated approaches to provided improved methods of performing highly parallel next generation sequencing.

SUMMARY

The present teachings provide a method for determining information about a sequence of nucleotides in a template using a first collection of at least 2 distinguishably labeled reversible di-nucleotide terminators, the method comprising;

(a) extending a primer along the template by incorporating a reversible di-nucleotide terminator to form an extension product, wherein the reversible di-nucleotide terminator is a member of the collection of distinguishably labeled reversible di-nucleotide terminator;

(b) detecting a label associated with the reversible di-nucleotide terminator;

(c) repeating steps (a) and (b) until an ordered list of reversible di-nucleotide terminator family names is obtained; and, (d) using the ordered list of reversible di-nucleotide terminator family names to eliminate one or more possibilities for the sequence of nucleotides of the template.

Additional methods, as well as compositions and kits are also provided.

DETAILED DESCRIPTION OF CERTAIN EMBODIMENTS

Figures 1A, 1B:
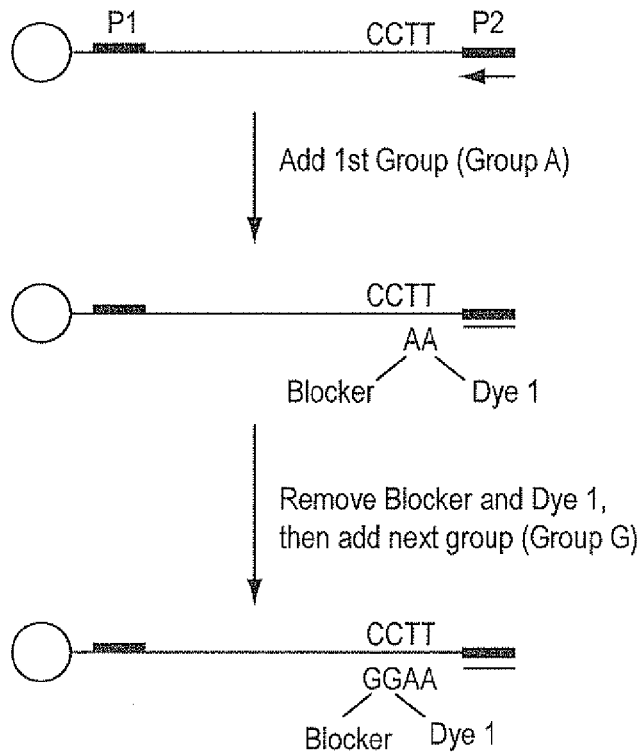
FIG. 1 shows one illustrative embodiment according to the present teachings.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in this application, this application controls.

The use of the singular includes the plural unless specifically stated otherwise. The word "a" or "an" means "at least one" unless specifically stated otherwise. The use of "or" means "and/or" unless stated otherwise. The use of "or" in the context of multiply dependent claims means the alternative only. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise. All ranges discussed herein include the endpoints and all values between the endpoints.

DEFINITIONS

As used herein, the term "nucleotide" includes native (naturally occurring) nucleotides, which include a nitrogenous base selected from the group consisting of adenine, thymidine, cytosine, guanine and uracil, a sugar selected from the group of ribose, arabinose, xylose, and pyranose, and deoxyribose (the combination of the base and sugar generally referred to as a "nucleoside"), and one to three phosphate groups, and which can form phosphodiester internucleosidyl linkages. Further, as used herein "nucleotide" refers to nucleotide analogs. Such analogs can have a sugar analog, a base analog and/or an internucleosidyl linkage analog. Additionally, analogs exhibiting non-standard base pairing are also included (see for example U.S. Pat. No. 5,432,272). Such nucleotide analogs include nucleotides that are chemically modified in the natural base ("base analogs"), chemically modified in the natural sugar ("sugar analogs"), and/or chemically modified in the natural phosphodiester or any other internucleosidyl linkage ("internucleosidyl linkage analogs"). In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases, e.g., adenine, guanine, cytosine, uracil, and thymine, and analogs of the naturally occurring nucleotide bases, e.g., 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2 ms6iA), N2-dimethylguanine (dmG), 7-methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, 2'-bromoribose, 2'iodoribose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352, and WO 99/14226). Exemplary LNA sugar analogs within a nucleic acid include, but are not limited to, the structures:

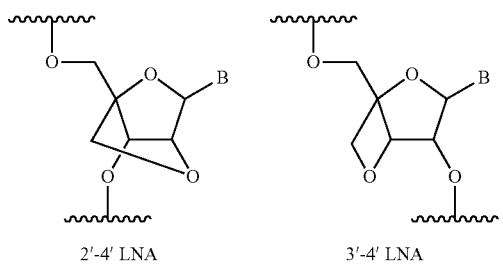

2'-4' LNA      3'-4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the $N^9$-position of the nucleotide base. When the nucleotide base is pyrimidine, e.g. C, T or U, the pentose sugar is attached to the $N^1$-position of the nucleotide base, except for pseudouridines, in which the pentose sugar is attached to the C5 position of the uracil nucleotide base (see, e.g., Kornberg and Baker, (1992) DNA Replication, $2^{nd}$ Ed., Freeman, San Francisco, Calif.).

One or more of the pentose carbons of a nucleotide may be substituted with a phosphate ester having the formula:

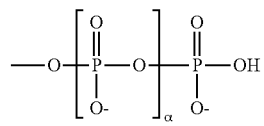

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof of the aforementioned. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see, e.g., Shabarova, Z. and Bogdanov, A. Advanced Organic Chemistry of Nucleic Acids, VCH, New York, 1994.

In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers which can be polymerized into nucleic acid analogs in which the DNA/RNA phosphate ester and/or sugar phosphate ester backbone is replaced with a different type of internucleotide linkage. Exemplary nucleic acid analogs include, but are not limited to, peptide nucleic acids.

Also included in the definition of "nucleotide analog" are the AAPNs described more fully below.

As used herein, the terms "polynucleotide", "oligonucleotide", and "nucleic acid" are used interchangeably and refer to single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, nucleotides and nucleotide analogs. A nucleic acid may comprise one or more lesions. Polynucleotides typically range in size from a few monomeric units, e.g. 5-40 when they are sometimes referred to in the art as oligonucleotides, to several thousands of monomeric nucleotide units. Unless denoted otherwise, whenever a nucleic acid sequence is represented, it will be understood that the nucleotides are in 5' to 3' order from left to right and that "A" denotes deoxyadenosine or an analog thereof, "C" denotes deoxycytidine or an analog thereof, "G" denotes deoxyguanosine or an analog thereof, and "T" denotes thymidine or an analog thereof, unless otherwise noted.

Nucleic acids may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deoxyribopolynucleotides according to the structural formulae below:

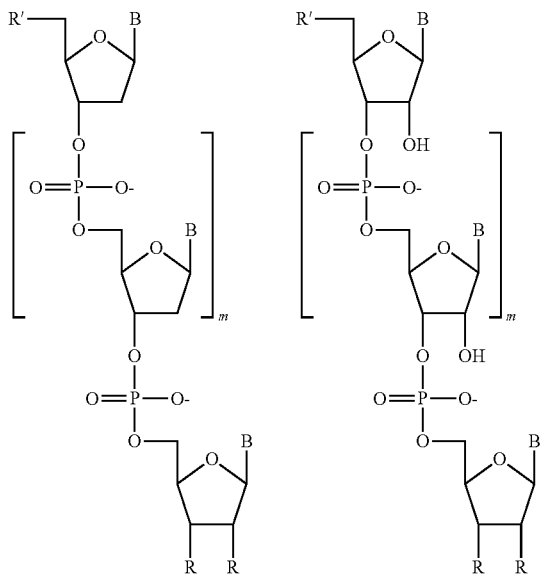

wherein each B is independently the base moiety of a nucleotide, e.g., a purine, a 7-deazapurine, a pyrimidine, or an analog thereof of the aforementioned. Each m defines the length of the respective nucleic acid and can range from zero to thousands, tens of thousands, or even more; each R is independently selected from the group comprising hydrogen, hydroxyl, halogen, —R", —OR", and —NR"R", where each R" is independently ($C_1$-$C_6$) alkyl or ($C_5$-$C_{14}$) aryl, or two adjacent Rs may be taken together to form a bond such that the ribose sugar is 2',3'-didehydroribose, and each R' may be independently hydroxyl or

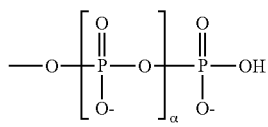

where α is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid", "polynucleotide", and "oligonucleotide" may also include nucleic acid analogs, polynucleotide analogs, and oligonucleotide analogs. The terms "nucleic acid analog", "polynucleotide analog" and "oligonucleotide analog" are used interchangeably, and refer to a polynucleotide that contains at least one nucleotide analog and/or at least one phosphate ester analog and/or at least one pentose sugar analog. A nucleic acid analog may comprise one or more lesions. Also included within the definition of nucleic acid analogs are nucleic acids in which the phosphate ester and/or sugar phosphate ester linkages are replaced with other types of linkages, such as N-(2-aminoethyl)-glycine amides and other amides (see, e.g., Nielsen et al., 1991, Science 254: 1497-1500; WO 92/20702; U.S. Pat. No. 5,719, 262; U.S. Pat. No. 5,698,685); morpholinos (see, e.g., U.S. Pat. No. 5,698,685; U.S. Pat. No. 5,378,841; U.S. Pat. No. 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114: 4006); 3'-thioformacetals (see, e.g., Jones et al., 1993, J. Org. Chem. 58: 2983); sulfamates (see, e.g., U.S. Pat. No. 5,470,967); 2-aminoethylglycine, commonly referred to as PNA (see, e.g., Buchardt, WO 92/20702; Nielsen (1991) Science 254: 1497-1500); and others (see, e.g., U.S. Pat. No. 5,817,781; Frier & Altman, 1997, Nucl. Acids Res. 25:4429 and the references cited therein). Phosphate ester analogs include, but are not limited to, (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate.

The terms "annealing" and "hybridization" are used interchangeably and refer to the base-pairing interaction of one nucleic acid with another nucleic acid that results in formation of a duplex, triplex, or other higher-ordered structure. In certain embodiments, the primary interaction is base specific, e.g., A/T and G/C, by Watson/Crick and Hoogsteen-type hydrogen bonding. Base-stacking and hydrophobic interactions may also contribute to duplex stability.

In this application, a statement that one sequence is the same as or is complementary to another sequence encompasses situations where both of the sequences are completely the same or complementary to one another, and situations where only a portion of one of the sequences is the same as, or is complementary to, a portion or the entire other sequence. Here, the term "sequence" encompasses, but is not limited to, nucleic acid sequences, templates, polynucleotides, oligonucleotides, and primers.

The term "primer" or "oligonucleotide primer" as used herein, refers to an oligonucleotide from which a primer extension product can be synthesized under suitable conditions. In certain embodiments, such suitable conditions comprise the primer being hybridized to a complementary nucleic acid and incubated in the presence of, for example, nucleotides, a polymerization-inducing agent, such as a DNA or RNA polymerase, at suitable temperature, pH, metal concentration, salt concentration, etc. In various embodiments, primers are 5 to 100 nucleotides long. In various embodiments, primers are 8 to 75, 10 to 60, 10 to 50, 10 to 40, or 10 to 35 nucleotides long.

The term "target nucleic acid" as used herein refers to an RNA or DNA that has been selected for detection. Exemplary RNAs include, but are not limited to, mRNAs, tRNAs, snRNAs, rRNAs, retroviruses, small non-coding RNAs, microRNAs, polysomal RNAs, pre-mRNAs, intronic RNA, and viral RNA. Exemplary DNAs include, but are not limited to, genomic DNA, plasmid DNA, phage DNA, nucleolar DNA, mitochondrial DNA, chloroplast DNA, cDNA, synthetic DNA, yeast artificial chromosomal DNA ("YAC"), bacterial artificial chromosome DNA ("BAC"), other extrachromosomal DNA, and primer extension products. Generally, the templates to be sequenced in the present teachings are derived from any of a variety of such target nucleic acids, themselves derived from any of a variety of samples.

The term "sample" as used herein refers to any sample that is suspected of containing a target analyte and/or a target nucleic acid. Exemplary samples include, but are not limited to, prokaryotic cells, eukaryotic cells, tissue samples, viral particles, bacteriophage, infectious particles, pathogens, fungi, food samples, bodily fluids (including, but not limited to, mucus, blood, plasma, serum, urine, saliva, and semen), water samples, and filtrates from, e.g., water and air.

As used herein, the term "amplification" refers to any method for increasing the amount of a target nucleic acid, or amount of signal indicative of the presence of a target nucleic acid. Illustrative methods include the polymerase chain reaction (PCR), rolling circle amplification (RCA), helicase dependant amplification (HDA), Nucleic Acid Sequence Based Amplification (NASBA), ramification amplification method (RAM), recombinase-polymerase amplification (RPA), multiple strand displacement amplification (MDA), and others. In some embodiments of the present teachings, amplification can occur in an emulsion PCR, containing primer-immobilized microparticles, as described for example in WO2006/084132, which is hereby incorporated by reference in its entirety for any purpose.

As used herein, the term "label" refers to detectable moieties that can be attached to nucleotides directly or indirectly to thereby render the molecule detectable by an instrument or method. For example, a label can be any moiety that: (i) provides a detectable signal; (ii) interacts with a second label to modify the detectable signal provided by the first or second label; or (iii) confers a capture function, e.g. hydrophobic affinity, antibody/antigen, ionic complexation. The skilled artisan will appreciate that many different species of labels can be used in the present teachings, either individually or in combination with one or more different labels. Exemplary labels include, but are not limited to, fluorophores, radioisotopes, Quantum Dots, chromogens, Sybr Green™, enzymes, antigens including but not limited to epitope tags, heavy metals, dyes, phosphorescence groups, chemiluminescent groups, electrochemical detection moieties, affinity tags, binding proteins, phosphors, rare earth chelates, near-infrared dyes, including but not limited to, "Cy.7.SPh.NCS," "Cy.7.OphEt.NCS," "Cy7.OphEt.CO$_2$Su", and IRD800 (see, e.g., J. Flanagan et al., Bioconjug. Chem. 8:751-56 (1997); and DNA Synthesis with IRD800 Phosphoramidite, LI-COR Bulletin #111, LI-COR, Inc., Lincoln, Nebr.), electrochemiluminescence labels, including but not limited to, tris(bipyridal) ruthenium (II), also known as Ru(bpy)$_3^{2+}$, Os(1,10-phenanthroline)$_2$bis(diphenylphosphino)ethane$^{2+}$, also known as Os(phen)$_2$(dppene)$^{2+}$ luminol/hydrogen peroxide, Al(hydroxyquinoline-5-sulfonic acid), 9,10-diphenylanthracene-2-sulfonate, and tris(4-vinyl-4'-methyl-2,2'-bipyridal) ruthenium (II), also known as Ru(v-bpy$_3^{2+}$), and the like.

As used herein, the term "fluorophore" refers to a label that comprises a resonance-delocalized system or aromatic ring system that absorbs light at a first wavelength and emits fluorescent light at a second wavelength in response to the absorption event. A wide variety of such dye molecules are known in the art, as described for example in U.S. Pat. Nos. 5,936,087, 5,750,409, 5,366,860, 5,231,191, 5,840,999, 5,847,162, and 6,080,852 (Lee et al.), PCT Publications WO 97/36960 and WO 99/27020, Sauer et al., J. Fluorescence 5(3):247-261 (1995), Arden-Jacob, Neue Lanwellige Xanthen-Farbstoffe für Fluoreszenzsonden and Farbstoff Laser, Verlag Shaker, Germany (1993), and Lee et al., Nucl. Acids Res. 20:2471-2483 (1992). Exemplary fluorescein-type parent xanthene rings include, but are not limited to, the xanthene rings of the fluorescein dyes described in U.S. Pat. Nos. 4,439,356, 4,481,136, 4,933,471 (Lee), U.S. Pat. No. 5,066,580 (Lee), U.S. Pat. Nos. 5,188,934, 5,654,442, and 5,840,999, WO 99/16832, EP 050684, and U.S. Pat. Nos. 5,750,409 and 5,066,580. Additional rhodamine dyes can be found, for example, in U.S. Pat. No. 5,366,860 (Bergot et al.), U.S. Pat. No. 5,847,162 (Lee et al.), U.S. Pat. No. 6,017,712 (Lee et al.), U.S. Pat. No. 6,025,505 (Lee et al.), U.S. Pat. No. 6,080,852 (Lee et al.), U.S. Pat. No. 5,936,087 (Benson et al.), U.S. Pat. No. 6,111,116 (Benson et al.), U.S. Pat. No. 6,051,719 (Benson et al.), U.S. Pat. Nos. 5,750,409, 5,366,860, 5,231,191, 5,840,999, and 5,847,162, U.S. Pat. No. 6,248,884 (Lam et al.), PCT Publications WO 97/36960 and WO 99/27020, Sauer et al., 1995, J. Fluorescence 5(3):247-261, Arden-Jacob, 1993, Neue Lanwellige Xanthen-Farbstoffe für Fluoresenzsonden and Farbstoff Laser, Verlag Shaker, Germany, and Lee et al., Nucl. Acids Res. 20(10):2471-2483 (1992), Lee et al., Nucl. Acids Res. 25:2816-2822 (1997), and Rosenblum et al., Nucl. Acids Res. 25:4500-4504 (1997), for example. Additional typical fluorescein dyes can be found, for example, in U.S. Pat. Nos. 5,750,409, 5,066,580, 4,439,356, 4,481,136, 4,933,471 (Lee), U.S. Pat. No. 5,066,580 (Lee), U.S. Pat. No. 5,188,934 (Menchen et al.), U.S. Pat. No. 5,654,442 (Menchen et al.), U.S. Pat. No. 6,008,379 (Benson et al.), and U.S. Pat. No. 5,840,999, PCT publication WO 99/16832, and EPO Publication 050684. In some embodiments, the dye can be a cyanine, phthalocyanine, squaraine, or bodipy dye, such as described in the following references and references cited therein: U.S. Pat. No. 5,863,727 (Lee et al.), U.S. Pat. No. 5,800,996 (Lee et al.), U.S. Pat. No. 5,945,526 (Lee et al.), U.S. Pat. No. 6,080,868 (Lee et al.), U.S. Pat. No. 5,436,134 (Haugland et al.), U.S. Pat. No. 5,863,753 (Haugland et al.), U.S. Pat. No. 6,005,113 (Wu et al.), and WO 96/04405 (Glazer et al.).

The labels of the present teachings can be attached directly to the base of the first nucleotide, directly to the base of the second nucleotide, and/or attached to the 3' carbon of the second nucleotide, using any of a variety of known-chemistries and linking groups.

The term "blocking moiety" refers to any structural feature which prevents the subsequent addition of di-nucleotides into a growing extension product. Such blocking can result from the absence of a hydroxyl group at the appropriate position, such as the 3' carbon. Generally, various blocking moieties are known in the art, and can be found for example in U.S. Pat. No. 6,664,079, U.S. Pat. No. 5,763,594, PCT Publication WO9106678, PCT Publication WO0053805, PCT Publication WO00050642, PCT Publication WO09305183, PCT Publication WO09735033, U.S. Pat. No. 6,232,465, U.S. Pat. No. 6,632,655, U.S. Pat. No. 6,087,095, U.S. Pat. No. 5,908,755, U.S. Pat. No. 5,302,509, all of which are hereby expressly incorporated by reference in their entirety for any purpose. Further, subsequent to incorporation of di-nucleotides, and detecting a label, any of a variety of methods of removing blocking groups from the 3' carbon, and removing the label, can be performed. For example, U.S. Pat. No. 6,664,079, describes one such method in the context of the label being attached to the base. As another example, U.S. Pat. No. 7,057,026 describes another method of removing a label and a blocking moiety from an incorporated nucleotide to allow for subsequent extension. As another example, published PCT Patent Application WO 2007/020457 A2 describes another method of removing a label and a blocking moiety from an incorporated nucleotide.

As used herein, the term "first nucleotide" refers to the upstream most nucleotide of a di-nucleotide. First nucleotides are also generally also known in the art as the 5'-most nucleotide. The nucleotide following the "first nucleotide" is referred to herein as a "second nucleotide."

As used herein, the term "reversible di-nucleotide terminator" refers to a compound comprising a first nucleotide connected to a second nucleotide by any of a variety of linkages, wherein the second nucleotide contains a removable blocking moiety. In some embodiments, the removable blocking moiety is attached to the 3' carbon.

As used herein, the term "shifted primer" refers to a primer which, relative to the position on a template at which another primer hybridizes, is shifted an appropriate number of nucleotides to allow for sequence decoding according to the present teachings. In some embodiments, the shift is an odd number of nucleotides. Typically in an embodiment in which di-nucleotides are incorporated and two nucleotides remain in the extension product following the cleavage reactions, the shifted primer will be shifted one nucleotide relative to the other primer, but shifts of any odd number of nucleotides are contemplated by the present teachings, including three, five, seven, etc. Such shifts can be shown as "n−1" in certain of the figures. It will be appreciated that the shift can be upstream or downstream relative to the position of the earlier primer.

As used herein, the term "suitable polymerase" refers to any polymerase that incorporates the di-nucleotide compounds of the present teachings into an extension product. Included are DNA-dependent DNA polymerases, RNA-dependent DNA polymerases, DNA-dependent RNA polymerases, and RNA-dependent RNA polymerases. Illustrative examples can be found, for example in U.S. Pat. No. 7,060,440, which is hereby incorporated by reference in its entirety for any purpose, and include the 543 amino acids of the C-terminus of Taq polymerase, Klenow (Exo-) DNA polymerase (commercially available from Fermentas) and Tth DNA polymerase (commercially available from Promega). Other polymerases can be used, as routine experimentation will provide.

Certain Exemplary Methods

Methods provided herein may be carried out in any order of the recited events that is logically possible, as well as the recited order of events. Standard techniques may be used for recombinant DNA, oligonucleotide synthesis, and tissue culture. Enzymatic reactions and purification techniques may be performed according to manufacturer's specifications and/or as commonly accomplished in the art and/or as described herein. The foregoing techniques and procedures may be generally performed according to conventional methods known in the art and as described in various general and more specific references, including but not limited to, those that are cited and discussed throughout the present specification. See, e.g., Sambrook et al. Molecular Cloning: A Laboratory Manual (2d ed., Cold Spring Harbor Laboratory Press, Cold Spring Harbor, N.Y. (1989)); Lehninger, Biochemistry (Worth Publishers, Inc.); Methods in Enzymology (S. Colowick and N. Kaplan Eds., Academic Press, Inc.); Oligonucleotide Synthesis (N. Gait, ed., 1984); A Practical Guide to Molecular Cloning ($2^{nd}$ Ed., Wily Press, 1988). Unless specific definitions are provided, the nomenclatures utilized in connection with, and the laboratory procedures and techniques of, biology, biochemistry, analytical chemistry, and synthetic organic chemistry described herein are those known and used in the art.

Sequencing by Successive Incorporation of Reversible Di-Nucleotide Terminators

A first aspect of the present teachings is presented in FIG. 1. Here in FIG. 1A, a template polynucleotide is shown attached to a bead. The template can have known ends that can be queried by primers, for example a "P1" end proximal to the bead and a "P2" end distal to the bead. A primer complementary to the P2 end can be hybridized to the template, thus forming a substrate suitable for polymerization with a suitable polymerase. For illustration, the template is shown containing a sequence CCTT from the 5' to 3' direction.

Proceeding with this example, a first group ("group A") of di-nucleotides can be presented, wherein each of the four di-nucleotides in the group A contains a different label (here, Dye 1-Dye 4, respectively). Such a group of four di-nucleotides can contain the same first nucleotide (here, A), but vary in the identity of the second nucleotide. Each of the four di-nucleotides in the group A can contain a blocker at the 3' position of the second nucleotide, such that incorporation of a given di-nucleotide into an extension product prevents addition of subsequent di-nucleotides. Further, each of the four di-nucleotides in the group A can contain a distinct label on the first nucleotide. Incorporation of a di-nucleotide, and subsequent detection of Dye 1 indicates incorporation of a 5'-Dye-1-A-A-Blocker-3'. Thus, the sequence of the first two nucleotides of the template is discovered to be 3'T5'.

The blocker present on the 3' position of the second nucleotide can now be removed, allowing a free 3' OH group to be formed, and the generation of an extendable terminus. Further, the label can be removed as well.

A next cycle can then be performed, for example using a group G, wherein each of the four di-nucleotides in the group contain a G at the 5' position. If the GG member of Group G is incorporated, as would be indicated by detection of Dye 4, the experimentalist then knows that the next two nucleotides in the template are CC. Following removal of the 3' blocker, and the label, the process can be repeated successively in a collection of cycles, each cycle comprising incorporation, detection, and removal of the label and the blocker. Of course, many rounds of presenting various groups will not produce a detectable signal, thus indicating the absence of the corresponding bases in the template.

Figure 2:
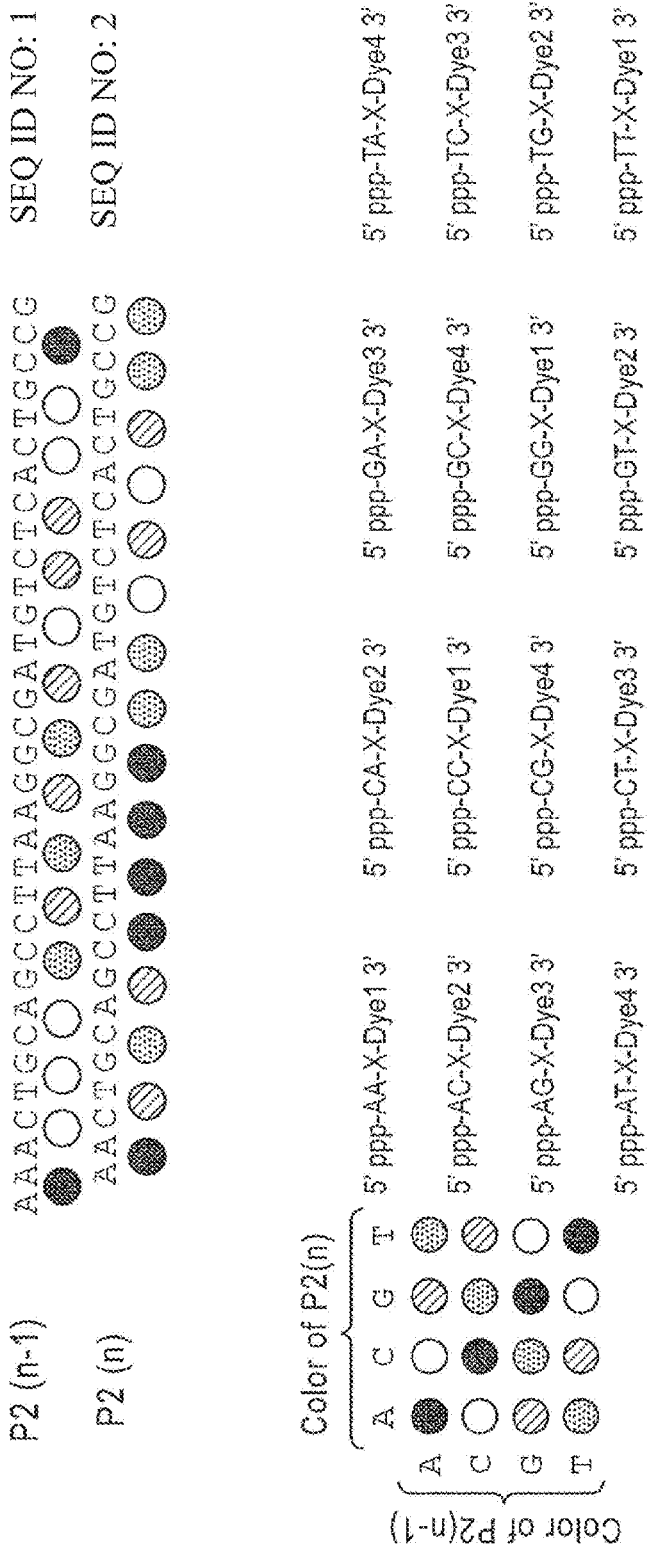
FIG. 2 shows one illustrative embodiment according to the present teachings.
Figure 2:
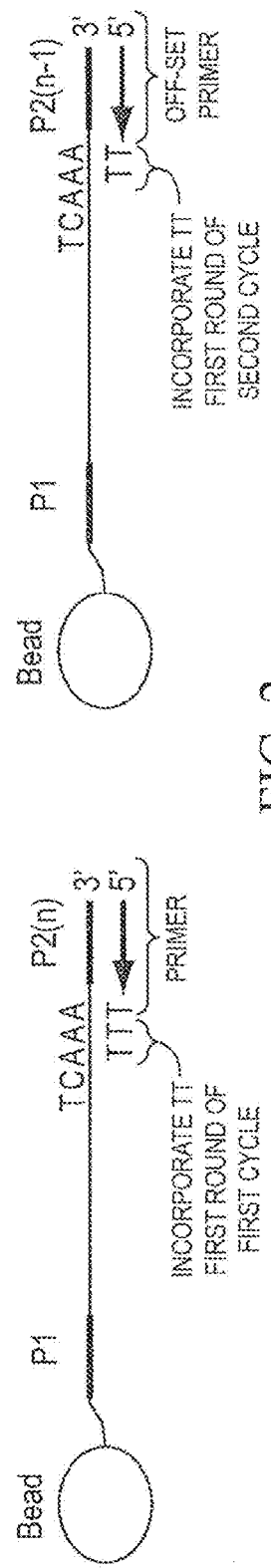
Figure 3A:
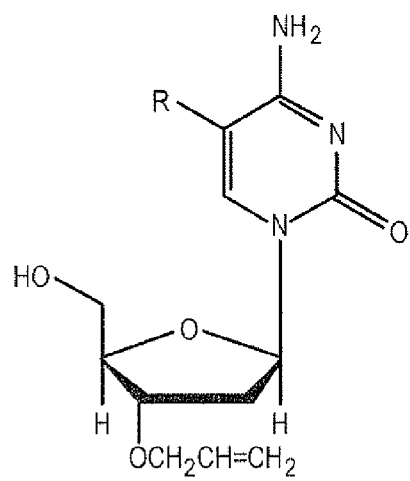
FIG. 3 shows one illustrative embodiment according to the present teachings.
Figure 3B:
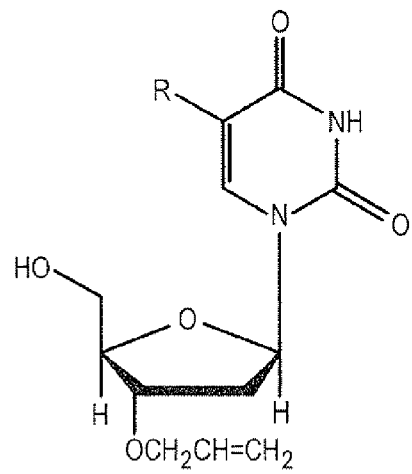
Figure 3C:
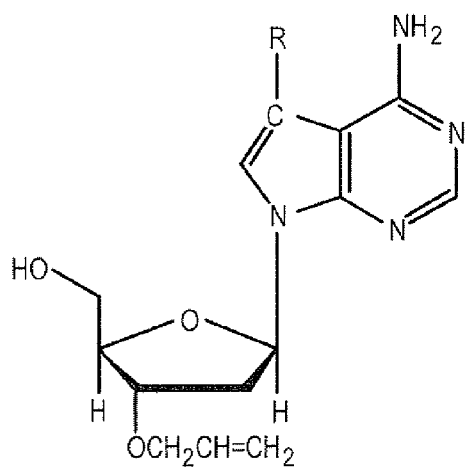
Figure 3D:
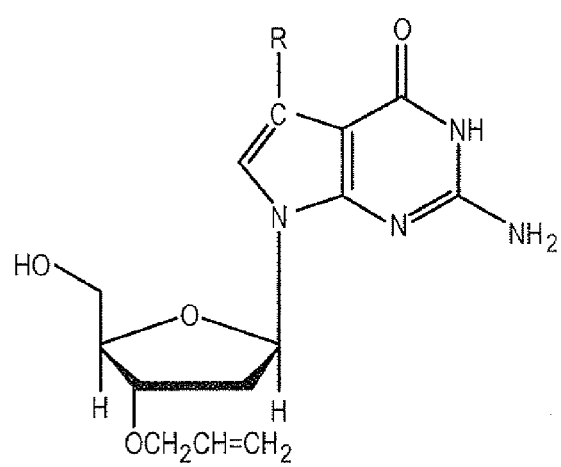

Two-Base Encoded Sequencing by Incorporating Reversible Di-Nucleotide Terminators A second aspect of the present teachings is presented in FIG. 2. Here, a template polynucleotide is shown attached to a bead. The template can have known ends that can be queried by primers, for example a "P1" end proximal to the bead and a "P2" end distal to the bead. A primer complementary to the P2 end can be hybridized to the template, thus forming a substrate suitable for polymerization with a suitable polymerase. For illustration, the template is shown containing a sequence TCAAA from the 5' to 3' direction.

Proceeding with this example, all sixteen possible reversible di-nucleotide terminators can be presented. There can be four "families" of reversible di-nucleotide terminators comprising the sixteen di-nucleotide terminators. Each of the four di-nucleotides in a family can contain the same label, but vary in the sequence of their two nucleotides. Each of the four reversible di-nucleotide terminators in a family can contain a reversible blacker at the 3' position of the second nucleotide, such that incorporation of a given reversible di-nucleotide terminator into an extension product prevents addition of subsequent di-nucleotides. Incorporation of a reversible di-nucleotide terminator, and subsequent detection of Dye 1 (solid fill circle) is indicative of the incorporation of one of the following four reversible di-nucleotide terminators:

5'-Dye-1-A-A-Blocker-3', or,
5'-Dye-2-T-T-Blocker-3', or,
5'-Dye-3-C—C-Blocker-3', or,
5'-Dye-4-G-G-Blocker-3'.

The blacker present on the 3' position of the second nucleotide can now be removed, allowing a free 3' OH group to be formed, and the generation of an extendable terminus. The label can also be removed. Removal of the cleaved label and cleaved blocker can be achieved with a washing step. A next cycle of incorporation can then be performed and the process can be repeated successively, to form a first "round" of several cycles of incorporation and deprotection, each cycle ultimately adding two nucleotides to the growing extension product. Eventually, the addition of subsequent di-nucleotides can be stopped, and the resulting extension product stripped from the template.

As provided at the bottom right of FIG. 2, a P2 primer, P2 n−1, can then be provided that is one nucleotide off-set compared to the first P2 primer, an example of a so-called "offset-primer". This off-set primer lacks the T that was present at the 3' end of the first P2 primer. Thereafter, successive cycles of di-nucleotide incorporation and deprotection can be repeated. These additions are shifted one nucleotide by the placement of the off-set primer. Determining the sequence of the template can be performed by compilation of the first round of di-nucleotide incorporation and detection cycles, with the second round of di-nucleotide incorporation and detection cycles. Such an approach is referred to as "two-base encoding".

In the present example, one can envision that in the first cycle of the first round, Dye 1 is detected. Detection of Dye 1 tells the experimentalist that one of the following di-nucleotides was incorporated: 5'AA3', or 5'CC3', or 5'GG3', or 5'TT3'. After the first round is completed, the extension product is stripped from the template. An off-set primer is hybridized to the template (P2(n−1)), and a first cycle of a second round can be performed. In the depicted embodiment, Dye 1 would be detected during this first cycle of the second round due to the incorporation of a TT dinucleotide. Thus, based on detection of the dye, the experimentalist would know that the di-nucleotide incorporated in this first cycle of the second round is one of the following: 5'AA3', or 5'CC3', or 5'GG3', or 5'TT3'.

Compiling the results of the first cycle of the first round, with the first cycle of the second round, provides the experimentalist with the information necessary to deduce the identity of the base in the first position encountered of the template: an A. This approach is shown pictorially in FIG. 2. As a result of these steps, the experimentalist collects and ordered list of probe family names. Here at the bottom of FIG. 2, detection of a solid circle incorporation event in the first cycle of the first round (TT incorporation) using primer P2(n), would eventually be followed by detection of a solid circle incorporation event in the first cycle of the second round (TT incorporation) using off-set primer P2(n−1). Said another way, if the first cycle of the first round yielded a solid circle, then only four possible di-nucleotides were incorporated during this cycle: 5'AA3', or 5'CC3', or 5'GG3', or 5'TT3'. Since the first cycle of the second round also produced detection of a solid circle, then only four possible di-nucleotides were incorporated during this cycle: 5'AA3', or 5'CC3', or 5'GG3', or 5'TT3'. Since the experimentalist knows that the off-set primer of the second round hybridized a single nucleotide away from the primer employed in the first round, then necessarily the identity of the first base sequenced of the template is an A. Repeating this process a sufficient number of times allows one to determine the entire sequence of the template.

Two-base encoding as applied in a ligation-based sequencing process is described in WO 2006/084132, which is hereby incorporated by reference in its entirety. As employed herein with polymerase-mediate extension of reversible di-nucleotide compounds, analogous analyses can be performed. For example, it will be appreciated that this two-base encoding, resulting in the ordered list of family names, contains a substantial amount of information, but not in a form that will immediately yield the sequence of interest. Further step(s), at least one of which involves gathering at least one item of additional information about the sequence, must be performed in order to obtain a sequence that is most likely to represent the sequence of interest. The sequence that is most likely to represent the sequence of interest can be referred to as the "correct" sequence, and the process of extracting the correct sequence from the ordered list of probe families is referred to as "decoding". It will be appreciated that elements in an "ordered list" as described above could be rearranged either during generation of the list or thereafter, provided that the information content, including the correspondence between elements in the list and nucleotides in the template, is retained, and provided that the rearrangement, fragmentation, and/or permutation is appropriately taken into consideration during the decoding process. The ordered list can be decoded using a variety of approaches. Some of theses approaches involve generating a set of at least one candidate sequence from the ordered list of probe family names. The set of candidate sequences may provide sufficient information to achieve an objective. In preferred embodiments one or more additional steps are performed to select the sequence that is most likely to represent the sequence of interest from among the candidate sequences or from a set of sequences with which the candidate sequence is compared. For example, in one approach at least a portion of at least one candidate sequence is compared with at least one other sequence. The correct sequence is selected based on the comparison. In certain embodiments, decoding involves repeating the method and obtaining a second ordered list of probe family names using a collection of probe families that is encoded differently from the original collection of probe families. Information from the second ordered list of probe families is used to determine the correct sequence. In some embodiments information obtained from as little as one cycle of extension, detection, cleavage, and —OH restoration using the alternately encoded collection of probe families is sufficient to allow selection of the correct sequence. In other words, the first probe family identified using the alternately encoded probe family provides sufficient information to determine which candidate sequence is correct.

The methods and compositions of the present teachings can be employed to sequence individual nucleic acids, so-called "single molecule" sequencing. Methods and composition of performing single molecule sequencing are described in Buzby et al., U.S. Published Patent Application 2007/0117104. This patent application describes methodology for single-molecule sequencing using mononucleotide 5'-triphosphates having 3'-hydroxylamine blockers that can be removed (see 0038-0040). In this application, the nucleobases have disulfide linkers to dyes that are also cleavable. Thus, the present teachings employing dinucleotide compounds can employ such chemistries and methods to achieve single molecule sequencing.

In some embodiments, polymerase mediated extension will not be completely efficient. Thus, a capping step can be employed to render un-extendable those nucleic acids that failed to incorporate during the polymerase treatment. For example, following the polymerase treatment, the unincorporated dinucleotides can be removed by washing, and conventional dideoxy-nucleotides can be added, such that only those nucleic acids that failed to incorporate earlier will be capped with a dideoxy nucleotide. Such capping serves the function of keeping all of the various nucleic acids undergoing sequencing in register. Various other capping approaches, both reversible and irreversible are known in the art, and can be found described for example in U.S. Pat. No. 6,664,079.
Sequencing by Incorporating Reversible Di-Nucleotide Terminators that Contain AAPNs.

Certain amino acid phosphoramidate nucleotides (AAPNs) have been found to function as substrates for DNA polymerization mediated by HIV reverse transcriptase or polymerase-mediated stepwise sequence of DNA, see for example Wu et al., N.A.R. 2007, September 18 epub, and Adelfinskaya et al., N.A.R. 2007; 35(15): 5060-72. These studies have demonstrated that systematic variation of amino acids in AAPNs, exemplified in the case of 3' deoxyadenosine, affords certain AAPNs that can function in primer extension reactions mediated by Therminator DNA polymerase. It has been noted that extending these observations to all four bases would allow evolution of a polymerase with enhanced efficiency for synthetic biology. Thus, in some embodiments of the present teachings use a set of A, G, C, and T AAPNs to screen existing, or new, site-directed mutant polymerases to obtain enzymes that can mediate stepwise sequencing with AAPNs that have 3'-blocking groups or 3'-unblocked base-modified groups. Such substrates can be synthesized by skilled artisans using conventional organic chemical methods, and such mutant enzymes can be obtained by skilled using conventional mutagenesis and expression methods. In some embodiments, the sequencing of RNA using RNA-polymerase mediated incorporation of ribose AAPNs is contemplated.

The AAPNs of the present teachings, along with appropriate polymerases, can be employed in various reversible dinucleotide terminator approaches, as described supra (e.g. FIG. 1 and FIG. 2).

Certain Exemplary Kits

The instant teachings also provide kits designed to expedite performing certain of the disclosed methods. Kits may serve to expedite the performance of certain disclosed methods by assembling two or more components required for carrying out the methods. In certain embodiments, kits contain components in pre-measured unit amounts to minimize the need for measurements by end-users. In some embodiments, kits include instructions for performing one or more of the disclosed methods. Preferably, the kit components are optimized to operate in conjunction with one another.

In various embodiments, the present teachings provide a kit for determining information about a sequence of nucleotides in a template polynucleotide comprising; a collection of distinguishably labeled reversible di-nucleotide terminator families, wherein each family comprises a collection of reversible di-nucleotide terminators, and wherein the collection of di-nucleotides in a family comprise the same label; and, a suitable polymerase. In some embodiments, the kit comprises microparticles. In some embodiments, the kit comprises a primer and a shifted primer.

EXAMPLES

Preparation of 16 possible di-nucleotides each having a 5'-triphosphate and 3'-blocker and dye-labeled nucleobase wherein said blocker and dye are allylic and simultaneously cleavable by palladium catalysis.

Example 1

Preparation of 4 3'-allyl nucleosides each having an N-trifluoroacetyl aminopropargyl linker attached to a nucleobase.

Compounds C-21, U-26, A-37 and G-42 are prepared as described in detail by Ju et al. (PNAS 2006, Supplementary Material). Such compounds are depicted in FIG. 3.

Example 2

Preparation of 16 possible di-nucleoside precursors each having a 5'-dimethoxytriyl(DMT) group.

Figure 4:
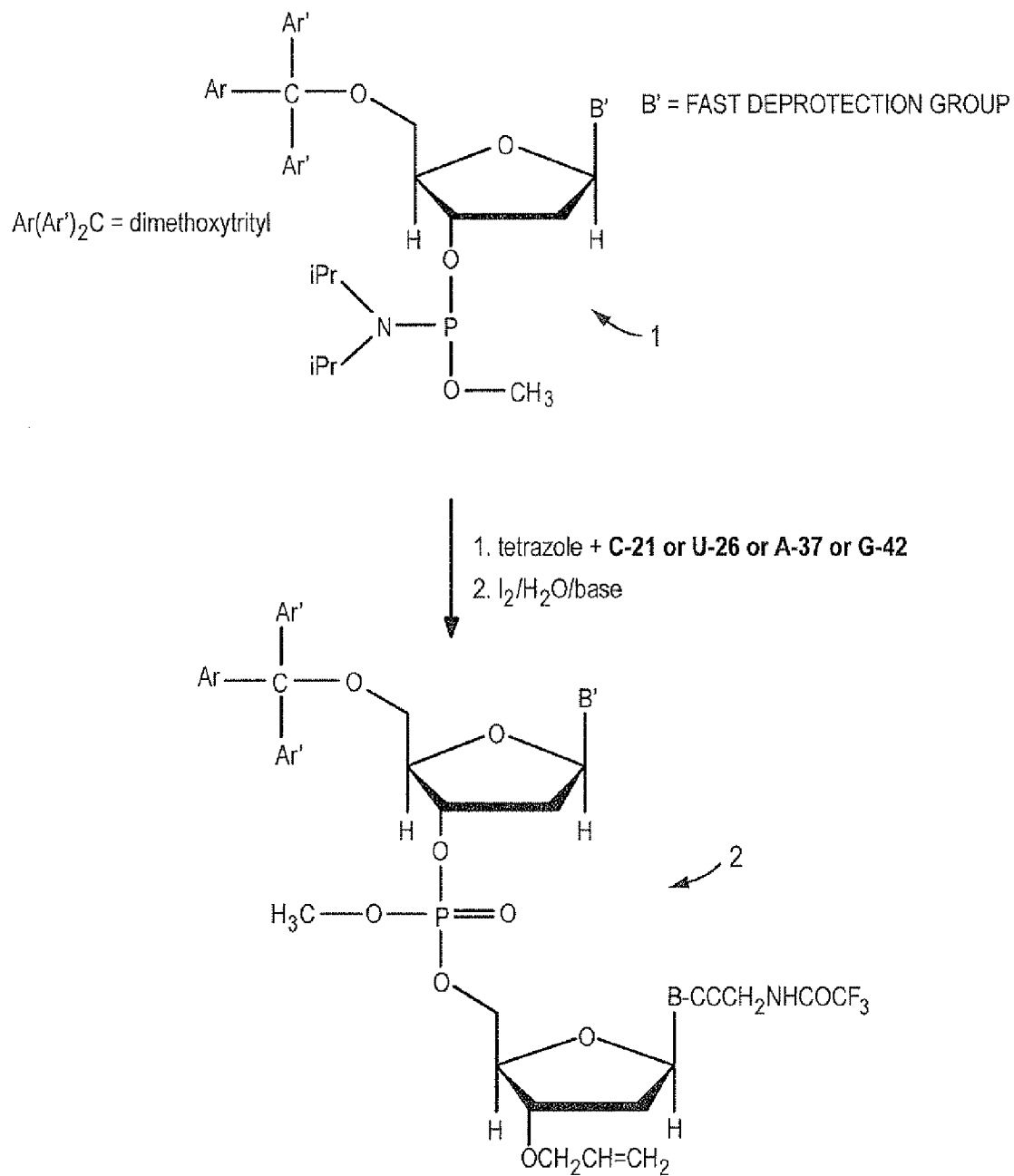
FIG. 4 shows one illustrative embodiment according to the present teachings.

Commercially available (Glen Research) nucleoside 5'-DMT 3'-phosphoramidites having nucleobases (B'=A, G, C but not U) protected by conventional fast-deprotection groups (1) are each coupled with C-21, U-26, A-37 and G-42 in acetonitrile using 1-equiv tetrazole, according to conventional procedures in solution phase (Chemical synthesis of DNA and DNA analogs. Caruthers, Marvin H. Accounts of Chemical Research (1991), 24(9), 278-84). Conventional oxidation with basic iodine/water and then DMT-assisted reversed-phase HPLC provides 16 possible di-nucleotide intermediates (2). This is depicted in FIG. 4.

Example 3

Preparation of 16 possible di-nucleoside precursors each having a 5'-triphosphate and 3'-blocker and nucleobase-attached propargyl amino group.

Figure 5:
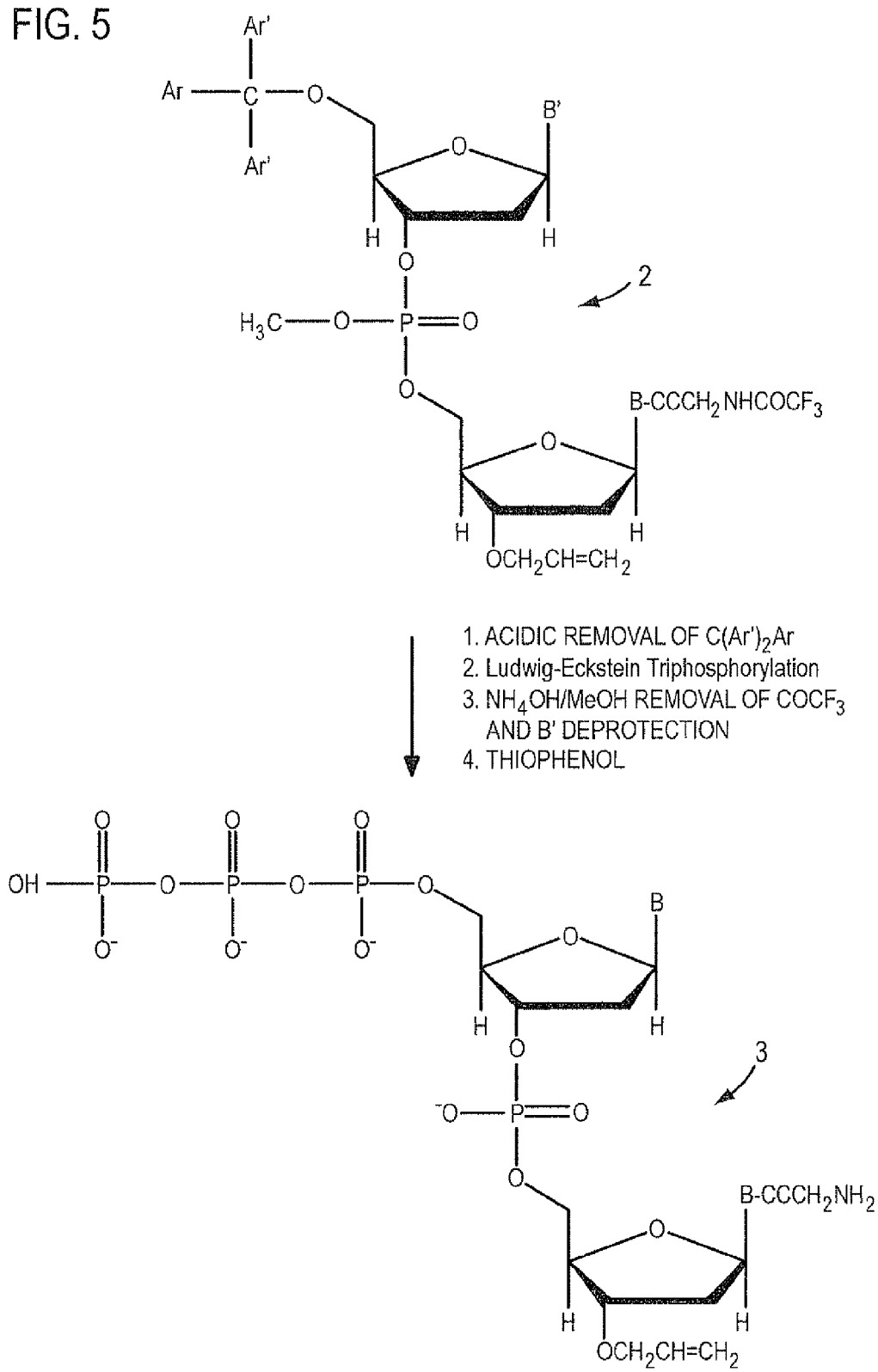
FIG. 5 shows one illustrative embodiment according to the present teachings.

As shown in FIG. 5, purified intermediates (2) obtained as described in Example 2 are each conventionally detritylated with mild acid and then subjected to Ludwig-Eckstein 5'-triphosphorylation (see for example, Rapid and efficient synthesis of nucleoside 5'-0-(1-thiotriphosphates), 5'-triphosphates and 2',3'-cyclophosphorothioates using 2-chloro-4H-1,3,2-benzodioxaphosphorin-4-one.Ludwig, Janos; Eckstein, Fritz. Journal of Organic Chemistry (1989), 54(3), 631-35). Subsequent treatment first with ammonium hydroxide in methanol and then with thiophenol provides crude material for anion-exchange HPLC to provide propargyl amino compounds (3).

Example 4

Preparation of 16 possible di-nucleotides each having a 5'-triphosphate and 3'-blocker and dye-labeled nucleobase wherein the blocker and dye are allylic and simultaneously cleavable by palladium catalysis.

Figure 6:
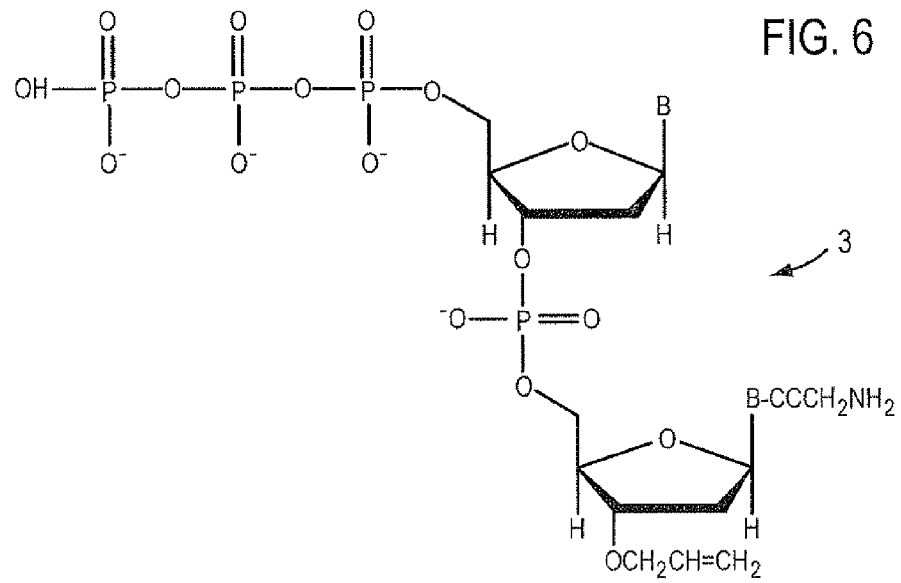
FIG. 6 shows one illustrative embodiment according to the present teachings.
Figure 6:
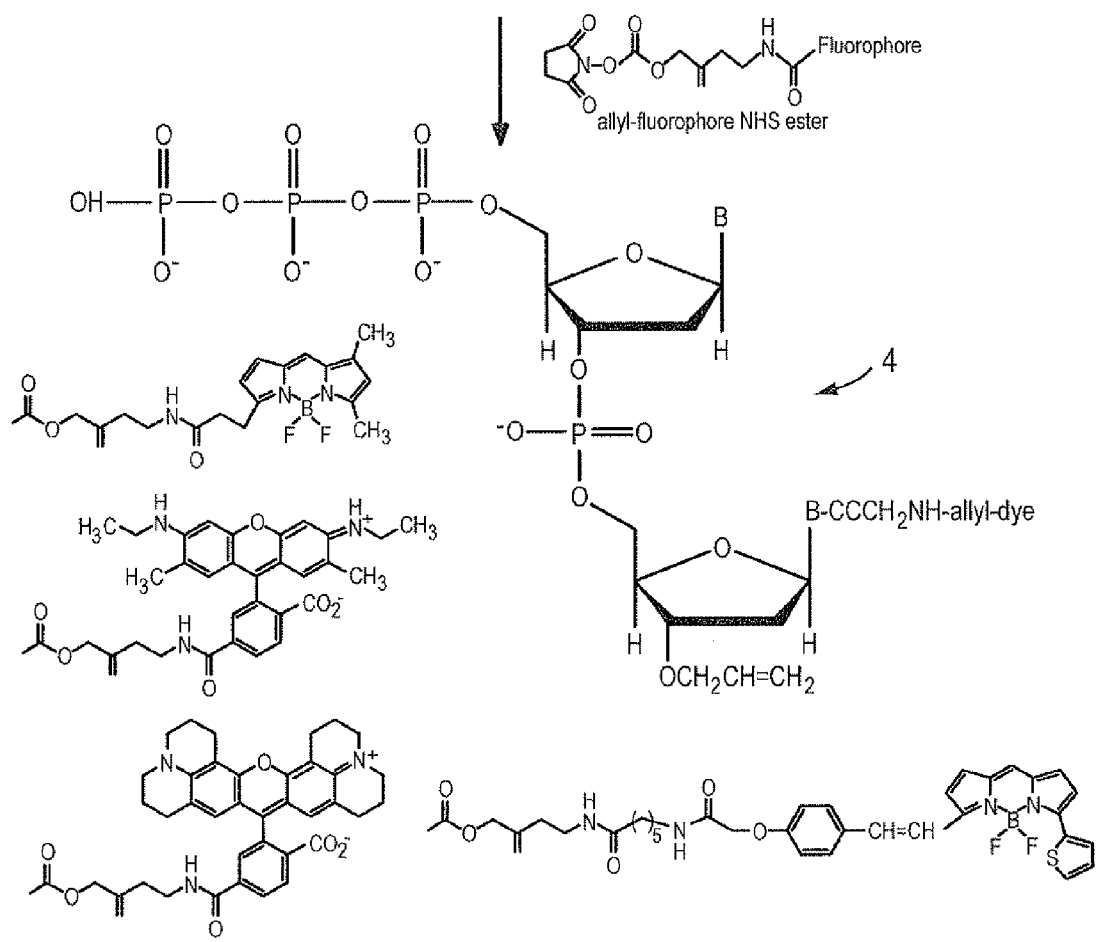

Propargyl amino compounds (3) obtained as described in Example 3 are each reacted with allyl-fluorophore N-hydroxy succinamides (NHS) shown in FIG. 6, wherein synthesis of the NHS compounds is described in Ju at al. (PNAS 2006, Supplementary Material), ultimately forming dinucleotide (4). Each member of the resultant set of target compounds is purified by anion-exchange HPLC. The set of 16 di-nucleotides 3 are color-coded as described in other sections of the present patent application. Exemplary dyes for such color coding are shown at the bottom of FIG. 6.

Additional methods for synthesizing dinucleotides useful in the present teachings can be found for example in Abramova et al., Biomedical and Medicinal Chemistry, 2008, "Design and synthesis of dinucleotide 5' triphosphates with expanded functionality", and Abramova et al., Biomedical and Medicine (2007) 15: 6549-6555).

While the present teachings have been described in terms of these exemplary embodiments, the skilled artisan will readily understand that numerous variations and modifications of these exemplary embodiments are possible without undue experimentation. All such variations and modifications are within the scope of the present teachings.

Further, the foregoing description and Examples detail certain preferred embodiments of the invention and describes the best mode contemplated by the inventors. It will be appreciated, however, that no matter how detailed the foregoing may appear in text, the present teachings may be practiced in many ways and should be construed in accordance with the appended claims and any equivalents thereof.

I claim:

1. A method for determining a sequence of a template polynucleotide, the method comprising:
   a) hybridizing a first primer to the template polynucleotide;
   b) contacting at least one labeled reversible di-nucleotide terminator and a DNA polymerase with the first primer to extend the first primer along the template by polymerase-mediated polymerization of the labeled reversible di-nucleotide terminator to form a first extension product, wherein the labeled reversible di-nucleotide terminator includes a first nucleotide connected to a second nucleotide and includes a detectable moiety linked to the first nucleotide and includes a blocking moiety linked to the second nucleotide;
   c) detecting the detectable moiety of the polymerized labeled reversible di-nucleotide terminator of step (b);
   d) identifying a probe family to which the polymerized labeled reversible di-nucleotide terminator in step (b) belongs, the probe family having a plurality of labeled reversible di-nucleotide terminators of varying sequence each having the same type of a detectable moiety;
   e) removing the blocking group on the polymerized labeled reversible di-nucleotide terminator of step (b) to generate a free 3' OH group;
   f) repeating steps (b), (c), (d), and optionally (e), to generate a first accumulated extension product;
   g) generating a set of candidate ordered series of the probe families which correlate with an ordered series of the polymerized labeled reversible di-nucleotide terminators in steps (b), (c) and (d); and
   h) determining the sequence of the template polynucleotide based at least in part on the first set of candidate ordered series of the probe families.

2. The method of claim 1, further comprising the step of removing the detectable moiety after step (c).

3. The method of claim 1, wherein the first type of nucleotide is adenosine, guanosine, cytidine, or thymidine.

4. The method of claim 1, wherein the second type of nucleotide is adenosine, guanosine, cytidine, or thymidine.

5. The method of claim 1, wherein the blocking moiety is linked to the 3C position on the second nucleotide in step (b).

6. The method of claim 1, wherein the detectable moiety is linked to the base or the 3C of the first nucleotide in step (b).

7. The method of claim 1, wherein the detectable moiety is a fluorophore.

8. The method of claim 1, wherein the polynucleotide template is immobilized to a bead.

9. The method of claim 1, further comprising polymerizing a dideoxynucleotide on the first extension product of step (b) so as to block further extension of the first or second extension product.

10. The method of claim 1, wherein the labeled reversible di-nucleotide terminator comprises an amino acid phosphoramidate nucleotide (AAPN).

11. A method for determining a sequence of a template polynucleotide, the method comprising:
   a) hybridizing a first primer to the template polynucleotide;
   b) contacting at least one labeled reversible di-nucleotide terminator and a DNA polymerase with the first primer to extend the first primer along the template by polymerase-mediated polymerization of the labeled reversible di-nucleotide terminator to form a first extension product, wherein the labeled reversible di-nucleotide terminator includes a first nucleotide connected to a second nucleotide and includes a detectable moiety linked to the first nucleotide and includes a blocking moiety linked to the second nucleotide, and wherein the labeled reversible di-nucleotide terminator is a member of a probe family having a plurality of labeled reversible di-nucleotide terminators each having the same type of a first nucleotide linked to the same type of a detectable moiety and having a different type of a second nucleotide;

c) detecting the detectable moiety of the polymerized labeled reversible di-nucleotide terminator of step (b);

d) identifying the probe family to which the polymerized labeled reversible di-nucleotide terminator in step (b) belongs;

e) removing the blocking group on the polymerized labeled reversible di-nucleotide terminator of step (b) to generate a free 3' OH group;

f) repeating steps (b), (c), (d), and optionally (e), to generate a first accumulated extension product;

g) generating a first set of candidate ordered series of the probe families which correlate with an ordered series of the polymerized labeled reversible di-nucleotide terminators in steps (b), (c) and (d); and h) determining the sequence of the template polynucleotide based at least in part on the first set of candidate ordered series of the probe families.

12. The method of claim 11, further comprising the step of removing the detectable moiety after step (c).

13. The method of claim 11, further comprising polymerizing a dideoxynucleotide on the first extension product of step (b) so as to block further extension of the first or second extension product.

14. A method for determining a sequence of a template polynucleotide, the method comprising:

a) hybridizing a first primer to the template polynucleotide;

b) contacting at least one labeled reversible di-nucleotide terminator and a DNA polymerase with the first primer to extend the first primer along the template by polymerase-mediated polymerization of the labeled reversible di-nucleotide terminator to form a first extension product, wherein the labeled reversible di-nucleotide terminator includes a first nucleotide connected to a second nucleotide and includes a detectable moiety linked to the first nucleotide and includes a blocking moiety linked to the second nucleotide;

c) detecting the detectable moiety of the polymerized labeled reversible di-nucleotide terminator of step (b);

d) identifying a probe family to which the polymerized labeled reversible di-nucleotide terminator in step (b) belongs, the probe family having a plurality of labeled reversible di-nucleotide terminators of varying sequence each having the same type of a detectable moiety;

e) removing the blocking group on the polymerized labeled reversible di-nucleotide terminator of step (b) to generate a free 3' OH group;

f) repeating steps (b), (c), (d), and optionally (e), to generate a first accumulated extension product;

g) generating a set of candidate ordered series of the probe families which correlate with an ordered series of the polymerized labeled reversible di-nucleotide terminators in steps (b), (c) and (d); and h) decoding the first set of candidate ordered series of the probe families to identify the most likely member of the first set of candidate ordered series.

15. The method of claim 14, further comprising the step of removing the detectable moiety after step (c).

16. The method of claim 14, further comprising polymerizing a dideoxynucleotide on the first extension product of step (b) so as to block further extension of the first or second extension product.

* * * * *